(12) United States Patent
Frevert

(10) Patent No.: US 8,748,151 B2
(45) Date of Patent: Jun. 10, 2014

(54) CLOSTRIDIAL NEUROTOXINS WITH ALTERED PERSISTENCY

(75) Inventor: Jurgen Frevert, Berlin (DE)

(73) Assignee: Merz Pharma GmbH & Co. KGaA, Frankfurt am Main (DE)

( * ) Notice: Subject to any disclaimer, the term of this patent is extended or adjusted under 35 U.S.C. 154(b) by 259 days.

(21) Appl. No.: 12/737,895

(22) PCT Filed: Aug. 28, 2009

(86) PCT No.: PCT/EP2009/006272
§ 371 (c)(1),
(2), (4) Date: Apr. 12, 2011

(87) PCT Pub. No.: WO2010/022979
PCT Pub. Date: Mar. 4, 2010

(65) Prior Publication Data
US 2011/0189158 A1    Aug. 4, 2011

Related U.S. Application Data

(60) Provisional application No. 61/190,558, filed on Aug. 29, 2008.

(30) Foreign Application Priority Data

Aug. 29, 2008  (EP) ..................... 08015287

(51) Int. Cl.
  *C12N 9/52*   (2006.01)
  *A61K 38/43*  (2006.01)
  *C07K 16/12*  (2006.01)
  *A61K 38/48*  (2006.01)

(52) U.S. Cl.
  CPC ............ *C07K 16/1282* (2013.01); *A61K 38/48* (2013.01)
  USPC ......................................... 435/220; 424/94.1

(58) Field of Classification Search
  None
  See application file for complete search history.

(56) References Cited

U.S. PATENT DOCUMENTS

| | | |
|---|---|---|
| 2003/0219462 A1 | 11/2003 | Steward et al. |
| 2004/0185525 A1 | 9/2004 | Nishimura et al. |
| 2006/0211619 A1 | 9/2006 | Steward et al. |
| 2008/0003241 A1 | 1/2008 | Marx et al. |
| 2008/0103098 A1 | 5/2008 | Specht |
| 2009/0118193 A1 | 5/2009 | Frevert et al. |
| 2011/0189158 A1 | 8/2011 | Frevert |

FOREIGN PATENT DOCUMENTS

| | | |
|---|---|---|
| EP | 1849801 | 10/2007 |
| JP | 2003070488 | 3/2003 |
| WO | WO 0074703 | 12/2000 |
| WO | 02/08268 | 1/2002 |
| WO | WO 02008609 | 10/2002 |
| WO | WO 03029458 | 4/2003 |
| WO | WO 2005063817 | 7/2005 |
| WO | WO 2006020748 | 2/2006 |
| WO | WO 2006027207 | 3/2006 |
| WO | WO 2006114308 | 11/2006 |
| WO | WO 2006133818 | 12/2006 |
| WO | WO 2007013839 | 2/2007 |
| WO | WO2007104567 | 9/2007 |
| WO | WO 2008000490 | 1/2008 |
| WO | WO 2009015840 | 2/2009 |

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Frampton et al. (Am. J. Clin. Dermatol., 4:709-725, 2003).*
Arndt et al. (J. Mol. Biol., 346:1083-1093, 2005).*
Zhang et al. (Gene 315:21-32, 2003).*
First Israeli Office Action for Patent Application No. 210845 of Nov. 20, 2012.
First Israeli Office Action for Patent Application No. 210845 of Nov. 20, 2012. Translation.
Binz, T., et al., "The complete sequence of botulinum neurotoxin type A and comparison with other clostridial nurotoxins" Journal of Biological Chemistry, Vo. 265, No. 16, p. 9153-9158, Jun. 5, 1990.
International Search Report with Written Opinion for PCT/EP2009/006272 of Oct. 27, 2009.
Berweck "Sonography-guided injection of botulinum toxin A in children with cerebral palsy", Neuropediatric 2002, 33:221-223.
Dasgupta, et al., "Purification and amino acid composition of type A botulinum neurotoxin", Toxicon 22:(3)415-424, 1984.
De Paiva, et al., Functional repair of motor endplates after botulinum neurotoxin type A poisoning: biphasic switch of synaptic activity between nerve sprouts and their parent terminals. Proc Natl Acad Sci U S A. 96(6):3200-3205, 1999.
Dressler, D (2000) Botulinum Toxin Therapy, Thieme Verlag, Stuttgart, New York.
Eleopra, et al., Botulinum neurotoxin serotype C: a novel effective botulinum toxin therapy in human. Neurosci Lett. 224(2):91-94, 1997.
Eleopra, et al., Botulinum neurotoxin serotypes A and C do not affect motor units survival in humans: an electrophysiological study by motor units counting. Clin Neurophysiol. 113(8):1258-1264, 2002.
European Search Report for EP08015287 dated Sep. 30, 2008.
Foran, et al., Evaluation of the therapeutic usefulness of botulinum neurotoxin B, C1, E, and F compared with the long lasting type A. Basis for distinct durations of inhibition of exocytosis in central neurons. J Biol Chem. 278(2):1363-71, 2003 [Epub Oct. 14, 2002].
Harris, Elv (Ed.), Angal, S. (Ed.), "Protein Purification Methods: A Practical Approach", Oxford University Press (Dec. 1989), ISBN-10: 019963002X, ISBN-13: 978-0199630028.

(Continued)

Primary Examiner — Brian J Gangle
(74) Attorney, Agent, or Firm — Hueschen and Sage

(57) ABSTRACT

The invention relates to a polypeptide comprising:
(a) a HC-domain or fragment thereof of the neurotoxic component of a clostridial toxin; and
(b) a first LC domain or fragment thereof of the neurotoxic component of a clostridial toxin; and
(c) at least one further LC domain or fragment thereof of the neurotoxic component of a clostridial toxin wherein the first and the at least one further LC domain may be the same or different from each other, and wherein each of said fragments of said first and of said at least one further LC domain still exhibits proteolytic activity.

11 Claims, No Drawings

(56) References Cited

OTHER PUBLICATIONS

Jones, et al., Journal of Immunological Methods 329(1-2):92-101, 2008.
Jurasinski, et al., Correlation of cleavage of SNAP-25 with muscle function in a rat model of Botulinum neurotoxin type A induced paralysis. Toxicon 39(9):1309-15, 2001.
Keller, JE. Neuroscience 139(2):629-37, 2006.
Montecucco, et al., The mechanism of action of tetanus and Botulinum neurotoxins. Arch Toxicol. 18 (Suppl.): 342-354, 1996.
Pearson, WR & Lipman DJ. PNAS 85:2444-2448, 1998.
Scopes, RK. "Protein Purification: Principles and Practice", Verlag: Springer, Berlin; Auflage: 3 Sub (Jan. 1994), ISBN-10: 0387940723, ISBN-13: 978-0387940724.
Simpson, LL, Ann Rev Pharmacol Toxicol. 44:167-93, 2004.
Walker, JM, Humana Press; "The Protein Protocols Handbook (Methods in Molecular Biology)", vol. 2 (Feb. 2002), ISBN-10: 0896039404, ISBN-13: 978-0896039407.
Yowler, et al., Biochemistry 43:9725-9731, 2004.
Dressler D (1995), Botulinum-Toxin-Therapie. Thieme Verlag, Stuttgart, New York.
Harris (Ed.), S. Angel (Ed.), "Protein Purification Methods: A Practical Approach", Oxford University Press (Dec. 1989).
John M. Walker, Humana Press; "The Protein Protocols Handbook (Methods in Molecular Biology)", vol. 2 (Feb. 2002).
Robert K. Scopes, "Protein Purification: Principles and Practice", Verlag: Springer, Berlin; Auflage: 3 Sub (Jan. 1994).
Bushara, K., Botulinum Toxin and Rhinorrhea, Otolaryngol. Head Neck Surg., 114(3):507, 1996.
Pakula, Andrew, A., et al. "Genetic analysis of protein stability and function", Annu. Rev. Genet., 1989, 23:289-310.
Protocol of Interview with RU Examiner for RU2011111700 dated Oct. 16, 2013.
Translation of Protocol of Interview with RU Examiner for RU2011111700.
Fernandez-Salas, et al. Is the light chain subcellular localization an important factor in botulinum toxin duration of action! Movement Disorders vol. 19, p. S23-S34, 2004.
Office Action from Australian Application 2009286973 dated Feb. 11, 2014.
Office Action from European Application 09778201.5 dated Jan. 27, 2014.
Tsai, et al., Targeting botulinum neurotoxin persistence by the ubiquitin-proteasome system, PNAS, vol. 107, No. 38, pp. 16554-16559, Sep. 21, 2010.
Wang, et al. Journal of Biological Chemistry 283(25):16993-17002, Jun. 20, 2008.

\* cited by examiner

CLOSTRIDIAL NEUROTOXINS WITH ALTERED PERSISTENCY

FIELD OF THE INVENTION

The present invention relates to Clostridial neurotoxins, e.g., botulinum neurotoxins, that are altered with regard to their protein structure in comparison to the corresponding wild-type neurotoxins. Said difference in protein structure results, inter alia, in a shifted time-period of activity, e.g. a prolonged activity or persistency.

BACKGROUND OF THE INVENTION

Chemodenervation refers to the use of an agent to prevent a nerve from stimulating its target tissue, e.g. a muscle, a gland or another nerve. Chemodenervation is for example performed with phenol, ethyl alcohol, or botulinum toxin. Chemodenervation is for example appropriate in patients with localized spasticity in one or two large muscles or several small muscles. It may be used to alleviate symptoms such as muscle spasm and pain, and hyperreflexia.

Chemodenervating agents block neuromuscular transmission at the neuromuscular junction, causing paralysis or paresis of the affected skeletal muscles. The term "paresis" is defined hereinunder as a condition typified by partial loss of movement, or impaired movement. This is accomplished either by acting presynaptically via the inhibition of acetylcholine (ACh) synthesis or release, or by acting postsynaptically at the acetylcholine receptor. Example of drugs that act presynaptically are botulinum toxin, tetrodotoxin and tetanus toxin.

The term "chemodenervation" also encompasses all effects which directly or indirectly are induced by the chemodenervating agent, therefore also comprising upstream, downstream or long-term effects of said chemodenervating agent. Therefore, presynaptic effects are also encompassed as well as postsynaptic effects; tissue effects and/or indirect effects via spinal or afferent neurons.

One chemodenervating agent, botulinum toxin, although being one of the most toxic compounds known to date, has in the past been used for the treatment of a large number of conditions and disorders, some of which are described in e.g. PCT/EP 2007/005754. Furthermore, commercial forms of botulinum toxin type A based on the botulinum toxin A protein complex are available under the tradename BOTOX® (*Clostridium botulinum* toxin type A purified toxin complex, (900 kDa), Allergan Inc.) and under the tradename DYSPORT® (*Clostridium botulinum* type A toxin-haemagglutinin complex; lpsen Ltd.), respectively. A pharmaceutical composition based on a higher purified toxin preparation and comprising the neurotoxic component of botulinum toxin type A free of complexing proteins in isolated form is commercially available in Germany from Merz Pharmaceuticals GmbH under the tradename XEOMIN® (incobotulinumtoxinA; *Clostridium botulinum* type A neurotoxin (150 kDa), free of Complexing proteins).

The anaerobic, Gram-positive bacterium *Clostridium botulinum* produces a potent polypeptide neurotoxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. Botulinum toxin A (BoNT/A) is the most lethal natural biological agent known to man. About 50 picograms of botulinum toxin (purified neurotoxin complex) serotype A is a $LD_{50}$ in mice. However, despite its toxic effects, botulinum toxin complex as well as the pure neurotoxin have been used as a therapeutic agent in a large number of diseases.

Botulinum toxins are released from lysed *Clostridium* cultures generally in the form of a protein responsible for the toxic properties of the botulinum toxin (the neurotoxic component) in association with other bacterial proteins (the non-toxic "complexing proteins" or "clostridial proteins"), which together form a toxin complex also designated "botulinum toxin complex". The botulinum toxin complex is metastable in nature, since its stability appears to depend on various factors such as e.g. salt concentration and/or pH. The molecular weight of the complex may vary from about 300,000 to about 900,000 Da i.e. from 300 kDa to about 900 kDa. The complexing proteins are, for example, various hemagglutinins. The proteins of this toxin complex are not toxic themselves but are believed to provide stability to the neurotoxic component and are responsible for oral toxicity in Botulinum intoxications. There are seven antigenically distinct serotypes of botulinum toxin, namely botulinum toxin A, B, C1, D, E, F and G. Wherever the botulinum toxin sero-type A, B, C1, D, E, F or G are mentioned, also known variants of the sero-types are encompassed, like serotypes A1, A2, A3, A4 etc.

The component of clostridial toxins responsible for its high toxicity is the neurotoxic component or protein (Mw≈150 kD, exact molecular weight depending of the serotype). The several different serotypes differ in their amino acid sequence, but possess all a similar structure: a light chain (LC) of approximately 50 kDa and a heavy chain (HC) of approximately 100 kDa, which may be linked by one or more disulfide bonds (for a review see e.g. Simpson L L, *Ann Rev Pharmacol Toxicol.* 2004; 44:167-93). The neurotoxic component of the botulinum toxin complex is initially formed as a single poly-peptide chain. In the case of serotype A, for example, proteolytic processing of the polypeptide results in an activated polypeptide in the form of a dichain polypeptide consisting of a heavy chain and a light chain, which are linked by a disulfide bond. In humans, the heavy chain mediates binding to pre-synaptic cholinergic nerve terminals and internalization of the toxin into the cell. The light chain is believed to be responsible for the toxic effects, acting as zinc-endopeptidase and cleaving specific proteins responsible for membrane fusion (SNARE complex) (see e.g. Montecucco C., Shiavo G., Rosetto O: The mechanism of action of tetanus and Botulinum neurotoxins. *Arch Toxicol* 1996; 18 (Suppl.): 342-354)).

The term "botulinum toxin" as used throughout the present application, refers to the neurotoxic component devoid of any other clostridial proteins, but also to the "botulinum toxin complex". The term "botulinum toxin" is used herein in cases when no discrimination between the toxin complex and the neurotoxic component is necessary or desired. "BoNT" or "NT" are common used abbreviations for botulinum neurotoxin or neurotoxin, respectively. The neurotoxic subunit of the botulinum toxin complex is referred in this document as the "neurotoxic component" or the "neurotoxic component free of complexing proteins". The production of the neurotoxic component of botulinum toxin type A and B are described, for example, in the international patent application WO 00/74703.

The several serotypes differ by their duration of therapeutic effect: The normal period of activity of botulinum toxin A drugs is, if injected intramuscular in humans, between 3 and 4 months. In single cases the period can even extend to more than 12 months. During the treatment of sweat glands, an activity of even 27 months has been reported (Bushara K., botulinum toxin and rhinorrhea, Otolaryngol. Head. Neck.

Surg., 1996; 114(3):507 and The Laryngoscope 109: 1344 1346:1999). The period of activity for botulinum toxin type C1 is comparable with the period of activity of botulinum toxin A (Eleopra et al., 1997 & 2002). Surprisingly the period of action is much shorter in rodents (e.g. mice) as compared to humans: Approximately 1-2 months for botulinum toxin A, 21 days for botulinum toxin B and only 4 days for botulinum toxin E (DePaiva et al., 1999, Juradinski et al., 2001).

Foran et al. analyzed in 2003 the time period of action in vitro on cerebellum-neurons of rats and found half-times of the inhibition of glutamate exocytosis for botulinum toxin A of more than 31 days; for botulinum toxin type C1 of more than 25 days; for botulinum toxin type B of approximately 10 days; for botulinum toxin type F of approximately 2 days and for botulinum toxin type E of only 0.8 days.

The time period of activity of botulinum toxin type A during e.g. the treatment of dystonias (e.g. Torticollis, Blepharospasmus) in humans is between 3 to 4 months. After this period the patient has to receive another injection of a botulinum toxin-containing drug. It would be of great advantage for the patient to prolong the time period of action of the neurotoxin. In doing so, the number of necessary injections per year would be reduced as well as the overall amount of *clostridial* proteins. This again would reduce the risk of the production of antibodies against the foreign protein. Therefore, the provision of a botulinum toxin with prolonged persistency would be desirable.

However, not always long-term paralyzation is desired. For example in certain cosmetical treatments sometimes only temporal "fine-adjustments" are required. To achieve a reduction of persistency the physician was restricted by the prior art methods to either the reduction of volume or the switch of serotype. These techniques proved to result in unsatisfying results and required profound knowledge both of the activity kinetics as well as the antigenicity of the different neurotoxin serotypes. Therefore, the provision of a neurotoxin with a "built-in" adjustment of persistency would be a major improvement.

US 2003/0219462, EP1849801 and WO 02/08268. disclose modified Botulinum toxins with added leucine- or tyrosine-based motifs to the native neurotoxin.

The idea for these alterations is based on the observation that certain leucine- or tyrosine-based motifs enable the localization of the light chain of the neurotoxic component of certain subtypes to the inner membrane of the target cell. This mechanism was hypothesized to change the persistency of certain light chains. Until now, however, the authors failed to provide any evidence for such an effect and newer experiments suggest that the whole hypothesis is inaccurate.

Furthermore, even if in certain cases an addition of motifs would lead to a membrane localization, such an approach is not applicable to modifications of Botulinum toxin A. This is because the native light chain of Botulinum toxin type A is already localized to the inner cell-membrane, therefore an additional tethering to the membrane does not provide any additional benefit.

Therefore the present invention followed a different path. As it has been found as disclosed in this application, the addition of a second light chain to the neurotoxin, which still possesses its proteolytic activity, leads to an alteration of the time period of activity. Depending on the combination of serotypes used, the time-period can be prolonged, allowing for the production of custom-tailored neurotoxins. It is envisaged to provide the physician with a range of neurotoxins, whose serotype is independent of their persistency, allowing for a more standardized treatment.

SUMMARY OF THE INVENTION

The present invention relates to clostridial neurotoxins, in one embodiment botulinum toxins, with increased or prolonged activity, i.e. persistency. Thus, in a first aspect the present application relates to a polypeptide comprising:
(a) a HC-domain or fragment thereof of the neurotoxic component of a clostridial toxin; and
(b) a first LC domain or fragment thereof of the neurotoxic component of a clostridial toxin; and
(c) at least one further LC domain or fragment thereof of the neurotoxic component of a clostridia toxin wherein the first and the at least one further LC domain may be the same or different from each other, and wherein each of said fragments of said first and of said at least one further LC domain still exhibits proteolytic activity.

In one embodiment the units and/or domains are connected via a bond, a peptide-linker, a chemical linker, a disulfide bond, or via a combination of two or more thereof.

In one embodiment the amino acid sequence of said LC and/or HC domain is at least 50% identical to the amino acid sequence of a neurotoxic component of botulinum toxin of serotype A, B, C, D, E, F or G.

In another embodiment the amino acid sequence of said LC and/or HC domain is at least 50% identical to the amino acid sequence of tetanus toxin (tetanospasmin).

In one embodiment the first and/or the second LC domain and/or the HC domain comprise at least one modification.

In one embodiment the modification is a mutation, in another embodiment a deletion, in yet another embodiment an insertion, in yet another embodiment an addition or in yet another embodiment an amino acid exchange or in a further embodiment a combination of two or more thereof.

In one embodiment, the invention relates to a polypeptide, wherein, the ganglioside-binding domain and/or the protein receptor binding-domain of the neurotoxin is modified such as to enhance the binding capacity compared to the wild-type neurotoxin from which the HC domain is derived.

In one embodiment the polypeptide is one selected from the group consisting of:
LCBoNT/A-LCBoNT/A-HCBoNT/A, LCBoNT/C-LCBoNT/A-HCBoNT/A, LCBoNT/B-LCBoNT/A-HCBoNT/A, LCBoNT/A-LCBoNT/C-HCBoNT/C, LCBoNT/C-LCBoNT/C-HCBoNT/C, LCBoNT/B-LCBoNT/C-HCBoNT/C and LCTeNT-LCBoNT/A-HCBoNT/A.

In yet another embodiment the modification is a chemical modification, whereas the chemical modification may be selected from the group comprising a phosphorylation, a pegylation, a glycosylation, a phosphorylation, a sulfatation, a methylation, an acetylation, a lipidation, a hydroxylation, an amidation or in a further embodiment a combination of two or more thereof. In a further embodiment the lipidation may be a myristoylation, plamitoylation, isoprenylation or linkage of glucosyl-phophatidylinositol or in a further embodiment a combination of two or more thereof.

The invention also discloses an antibody specific for any of the above mentioned polypeptides.

The invention also discloses a nucleic acid encoding for any of the above mentioned polypeptides. The invention discloses furthermore a vector comprising said nucleic acid or fragments thereof. A host cell comprising said nucleic acid or said vector is also disclosed herein.

The invention also discloses a method for producing a polypeptide comprising the steps of cultivating the host cell as mentioned before, producing and purifying said polypeptide encoded by said nucleic acid or vector and, optionally, formulating said polypeptide in a pharmaceutical composition.

The invention furthermore discloses a composition comprising the above mentioned polypeptide or the polypeptide obtainable by the above mentioned method. The invention also discloses said composition further comprising a pharmaceutically acceptable carrier. In another embodiment the composition further comprises a pH buffer, an excipient, a cryoprotectant, a preservative, an analgesic, a stabilizer or any combination thereof. In one embodiment the composition is provided as a lyophilisate. In another embodiment the composition is provided as a solution.

The invention also discloses said compositions for use in a therapeutic treatment.

The invention also discloses the use of said compositions for the manufacture of a medicament for therapeutic treatment.

In one embodiment said therapeutic treatment comprises treatment of focal dystonia, spasticity or a condition which can be treated by suppressing secretion.

The invention also discloses the use of said composition for cosmetic treatment. Within such cosmetic treatment, it may very well be that in particular mammals are treated who psychologically suffer from the condition, e.g. wrinkles, or glabella frown line, that is to be treated.

DETAILED DESCRIPTION OF THE INVENTION

The present invention relates to:
A polypeptide comprising:
(a) a HC domain of the neurotoxic component or fragment thereof of a clostridial toxin; and
(b) a first LC domain or fragment thereof, and
(c) at least one further LC domain or fragment thereof, wherein the first and second LC domain may be the same or different from each other In particular the invention relates to a polypeptide comprising:
(a) a HC-domain or fragment thereof of the neurotoxic component of a clostridial toxin; and
(b) a first LC domain or fragment thereof of the neurotoxic component of a clostridial toxin; and
(c) at least one further LC domain or fragment thereof of the neurotoxic component of a clostridial toxin wherein the first and the at least one further LC domain may be the same or different from each other, and wherein each of said fragments of said first and of said at least one further LC domain still exhibits proteolytic activity.

Surprisingly, it has been found that the addition of one or more (further) light chains (LC) to a polypeptide comprising at least one heavy chain (HC) and at least one light chain (LC) of the neurotoxic component of clostridial neurotoxins, as defined above, results in a polypeptide with increased i.e. prolonged persistency of the toxin activity as compared to the wild-type toxin.

Without being bound to theory it is hypothesized that, after binding to the cell surface, both light chains are translocated into the cell, increasing the concentration of proteolytic active proteins in the cell, thereby both increasing the activity as well as the persistency of the neurotoxin.

That is, if a long persistency of the polypeptide of the invention is desired, the artisan is instructed to use certain combinations of HC and LC domains, e.g. LC domains derived from serotypes with long persistency. In other embodiments a shorter persistency is achieved by combining certain other LC domains or fragments, e.g. such derived from serotypes with shorter persistency.

The term "persistency" as used herein describes the time period of action of a neurotoxic component. In general this is the time period until the active agent shows only half of its activity compared to its starting activity. Therefore, the term "persistency" can be used synonymously with the term "half-life of activity" or the term "half-life of metabolic stability" which defines the time point where just one half of the starting protein-concentration is active due to metabolic processes, i.e. the half-life until the protein is metabolized. Since the half-life of the protein correlates with the duration of the therapeutic effect, the term "persistency" also indirectly encompasses the time duration of interference or influence caused by a neurotoxic component with a cellular function.

The skilled person knows various assays for determining persistency. According to the teaching of the present invention, persistency may be determined with a mouse running assay (Keller J E., 2006, Neuroscience. 139(2):629-37). This assay allows correlating persistency with movement activity. Alternatively, persistency may be determined with a SNAP-25 cleavage assay, which allows correlating proteolytic activity with persistency. The effect of an increased persistency is fulfilled, if an increase in persistency can be determined in one of the assays described above, wherein the SNAP-25 cleavage assay is preferred.

The term increased persistency and prolonged persistency are used herein exchangeable.

For determining the impact of an additional LC chain, or LC chain fragment, on the polypeptide of the invention with regard to persistency, the polypeptide of the invention is compared to a corresponding polypeptide lacking said additional (further) LC chain. This may, for example, be a polypeptide of the invention from which the additional LC chain has been deleted. Any of the persistency assays known to the person skilled in the art may be used for determining persistency. In one embodiment, persistency is determined as described herein above or in the examples illustrating the invention.

In another embodiment the prolongation of the persistency of short acting neurotoxin serotypes is envisaged. For example the persistency of serotype E can be prolonged by adding light chains of longer active serotypes like for example serotype A, thereby creating a neurotoxin with a similar persistency as the wild-type botulinum toxin A. Since most of the antigenic epitopes of the neurotoxin are situated on the heavy chain subunit, this modification can be used to apply a neurotoxin in patients which have developed an immune response against a certain serotype. Thereby combining the advantage of providing a different serotype by maintaining the previous time period of activity.

As indicated above, the terms "HC-domain" and "LC-domain" refer to the heavy chain respectively light chain of the neurotoxic component of the neurotoxin either of wild-type or recombinant origin. Furthermore, in some embodiments the HC and/or LC domains are derived from different serotypes and/or different toxins. Within this definition also fragments of the light chain and heavy chain are encompassed. The HC- and LC-domain can additionally be further subdivided into sub-domains.

The term "further LC domain or fragment" thereof, as used herein refers to a one or more, e.g. second LC domain. According to the teaching of the present invention, the polypeptide of the invention may contain further additional LC domains or fragments thereof. For example, the polypeptide of the invention may comprise the HC domain of the neurotoxic component of a clostridial toxin and a first LC domain or fragment thereof and a second LC domain or fragment thereof and a third LC domain or fragment thereof.

In one embodiment, said fragment of said first and said further LC domain exhibits the proteolytic activity of the wild type LC.

To achieve said effect of increased persistency no additional leucine- or tyrosine-based motif (as disclosed in US 2003/0219462, EP1849801 and WO 02/08268) is neither needed nor desired. Therefore, in one embodiment, the additional light chain does not possess any of said motifs.

In one embodiment the modified neurotoxin does not contain a leucin-based motif comprising seven amino acids, wherein the first five amino acids starting from the amino-terminal of the leucine-based motif form a "quintet of amino acids" and the following two amino acids form a "dublet of amino acids" and wherein the quintet of amino acids comprises at least one amino acid selected from a group consisting of glutamate and aspartate; and the duplet of amino acids comprises at least one amino acid selected from from a group consisting of isoleucine and leucine.

In another embodiment the modified neurotoxin does not contain any of the sequences FEFYKLL (SEQ ID NO:1), EEKRAIL (SEQ ID NO:2), EEKMAIL (SEQ ID NO:3), SERDVLL (SEQ ID NO:4), VDTQVLL (SEQ ID NO:5), AEVQALL (SEQ ID NO:6), SDKQNLL (SEQ ID NO:7), SDRQNLI (SEQ ID NO:8), ADTQVLM (SEQ ID NO:9), SDKQTLL (SEQ ID NO:10) SQIKRLL (SEQ ID NO:11), ADTQALL (SEQ ID NO:12) and NEQSPLL (SEQ ID NO:13).

The term "the same as" used herein refers to an LC domain With identical amino acid sequence, i.e. with 100% amino acid sequence Identity. Therefore, e.g. a second LC domain, as used herein, which is "the Same" means it is identical in amino acid sequence to said first LC domain. On the other hand, a second LC domain which is "different" refers to a sec-ond LC domain which has a sequence identity of less than 100%, i.e. for ex-ample 99.95% or less compared to the first LC domain. A "different LC do-main" is an LC domain of a different serotype or an LC domain with an amino acid sequence that is different from the first LC domain, e.g. one with an amino acid substitution. Another example of a different LC domain is an LC domain with a truncation at the N- or C-terminus or with an internal deletion. Yet another example of a different LC domain is an LC domain with a chemi-cal modification. A "different LC domain" may therefore be derived from the same or different serotype, Respectively compared to the first LC domain. The above also applies to a "third" or any other additional LC domain.

In another embodiment the modified neurotoxin does not contain any of the sequences FEFYKLL, EEKRAIL, EEK-MAIL, SERDVLL, VDTQVLL, AEVQALL, SDKQNLL, SDRQNLI, ADTQVLM, SDKQTLL, SQIKRLL, ADTQALL and NEQSPLL.

The term "the same as" used herein refers to an LC domain with identical amino acid sequence, i.e. with 100% amino acid sequence identity. Therefore, e.g. a second LC domain, as used herein, which is "the same" means it is identical in amino acid sequence to said first LC domain. On the other hand, a second LC domain which is "different" refers to a second LC domain which has a sequence identity of less than 100%, i.e. for example 99.95% or less compared to the first LC domain. A "different LC domain" is an LC domain of a different serotype or an LC domain with an amino acid sequence that is different from the first LC domain, e.g. one with an amino acid substitution. Another example of a different LC domain is an LC domain with a truncation at the N- or C-terminus or with an internal deletion. Yet another example of a different LC domain is an LC domain with a chemical modification. A "different LC domain" may therefore be derived from the same or a different serotype, respectively compared to the first LC domain. The above also applies to a "third" or any other additional LC domain.

In one embodiment the serotypes of all HC and LC domains are from botulinum toxin type A, in another embodiment the second light chain is of serotype C1. However, it is clear to the person skilled in the art, that all possible combinations of serotypes A, B, C1, D, E, F and G are covered by this application and the skilled person is able to choose an appropriate combination based on the published persistency of the different serotypes. Neither the combination of serotypes nor the number of used heavy and light chains is restricted by this invention. Therefore, in another embodiment longer fusion proteins, i.e. fusion protein with more than three subunits are envisaged, e.g. protein-concatemers comprising three, four, five, six, seven, eight, nine or ten LC domains.

The HC and LC domains of for example the neurotoxin A of *C. botulinum* comprise different subdomains. The HC domain, for example comprises three sub-domains, i.e. amino-terminal 50 kDa translocation sub-domain $HC_N$ with the subsequent 25 kDa $HC_{CN}$-sub-domain and the 25 kDa $HC_{CC}$-sub-domain located carboxy-terminally. Taken together, the $HC_N$-, $HC_{CN}$ and $HC_{CC}$-domains are designated as HC-domain.

The respective amino acid ranges of the respective domains are shown for the different BoNT/A serotypes and its variations in table 1.

TABLE 1

Database accession numbers of the amino acid sequences of botulinum neurotoxin A subtypes 1-4 and amino acid ranges of the respective domains.

| BoNT/A subtype | Genbank # | Amino acids # | $HC_N$ | HC $HC_C$ $HC_{CN}$ | $HC_{CC}$ |
|---|---|---|---|---|---|
| A1 | AAA23262 | 1296 | 449-866 | 867-1091 | 1092-1296 |
|  | AAM75961 |  |  |  |  |
|  | AAQ06331 |  |  |  |  |
|  | BTCLAB |  |  |  |  |
|  | ABP48105 |  |  |  |  |
|  | ABP48106 |  |  |  |  |
|  | ABO68834 |  |  |  |  |
|  | ABO68833 |  |  |  |  |
|  | ABD65472 |  |  |  |  |
|  | AAQ06331 |  |  |  |  |
|  | P10845 | 1296 | 449-866 | 867-1091 | 1092-1296 |
|  | CAA36289 | 1296 | 449-866 | 867-1091 | 1092-1296 |
| A2 | CAA51824 | 1296 | 449-866 | 867-1091 | 1092-1296 |
|  | I40645 |  |  |  |  |
|  | Q45894 |  |  |  |  |
|  | AAX53156 |  |  |  |  |
|  | ABC26002 | 1296 | 449-866 | 867-1091 | 1092-1296 |
| A3 | ABA29017 | 1292 | 445-862 | 863-1087 | 1088-1292 |
| A4 | ABA29018 | 1296 | 449-866 | 867-1091 | 1092-1296 |

The term "fragment of the LC domain", as used herein, refers to a fragment of the LC domain with biological activity. As used herein, a fragment with biological activity is a fragment which (still) exhibits the proteolytic activity preferably of the wild-type LC, i.e. which is capable of cleaving a polypeptide of the SNARE complex such as e.g. syntaxin, SNAP-25 or synaptobrevin. Accordingly, biological activity may be tested e.g. by a SNAP-25 protease assay, $LD_{50}$-Assay, HDA-Assay, and the like. Therefore, any LC-domain, which shows proteolytic activity of more than 10%, 20%, 30%, 40%, 50%, 60%, 70%, 80%, 90% and up to 100% of the corresponding wild-type LC-domain in a SNAP-25 assay is considered "biological active" or "to exhibit proteolytic activity" within the scope of this invention.

A suitable SNAP-25 assay is for example the "GFP-SNAP25 fluorescence release assay" (WO/2006/020748) or the "improved SNAP25 endopeptidase immuno-assay" (Jones et al., Journal of Immunological Methods, Volume 329, Issues 1-2, 1 Jan. 2008, Pages 92-101).

A "fragment of the HC domain", as used herein, refers to a fragment of the HC domain with biological activity. More specific, this is a fragment which is still capable of binding to the native HC domain receptor, from which it is derived. Moreover, said fragment is also a fragment capable of translocating an LC domain attached to it.

Fragments, therefore, are e.g. polypeptides of which 1, 2, 3, 5, or up to 10, 50, or 100 amino acids have been deleted. Wherein the deletion can be a truncation at the C- or N-terminus or an internal deletion.

In some embodiments the HC and/or LC domains are additionally modified by for example a mutation, a deletion, an insertion, an addition or an amino acid exchange. In further embodiments the HC and/or LC are additionally be chemically modified, for example by a phosphorylation, a pegyiation, a glycosylation, a phosphorylation, a suifatation, a methylation, an acetylation, a lipidation (myristoylation, palmitoylation, isoprenylation, linkage of glucosyl-phophatidylinositol), a hydroxylation, an amidation or any other suitable modification. Additionally the ganglioside-binding domain and/or the binding-domain of the neurotoxin are in one embodiment modified such as to enhance the binding capacity compared to the wild-type neurotoxin from which the HC domain is derived. In some embodiments, the HC and/or LC comprise a tag-sequence, i.e. another amino acid sequence, which allows a simplified purification procedure.

The term "purification method" encompasses all methods known in the art for protein purification. Examples for purification methods for neurotoxins are the publications of Das-Gupta & Sathyamoorthy and WO2000074703 which are incorporated by reference herein. For further guidance of protein purification methods useful for the purification of recombinant neurotoxic components, reference is made to the documents of Walker et al., 2002; Harris et al. 1989 and Scopes et al., 1994, which are cited in the section "Literature" below.

The term "production of the polypeptide" encompasses all steps necessary for the production of the polypeptide, i.e. for example creation of the encoding nucleic acid, incorporation said nucleic acid into a vector, expression of the polypeptide in vitro and/or a host cell, modifications of the polypeptide in vivo and/or in vivo, purification of the polypeptide and/or production of a composition containing said polypeptide. Thereby the term "expression" or "gene expression" is defined herein as the process by which the inheritable information in a gene, such as the DNA sequence, is made into a functional gene product, such as protein or RNA.

In one embodiment it is envisaged to incorporate into the poly-peptide of the present invention additional receptor binding sites to provide a neurotoxin which possesses, besides an increased persistency, additional characteristics allowing for new applications, e.g. a neurotoxin with cell-specific binding sites suitable for example for the treatment of allergies or pain (WO 2007/13839). Alternatively, the native binding site located within the HC domain may be altered in order to target the polypeptide of the present invention to specific cell types. In a more particular example, the HC domain of the present invention.

In one embodiment the second light chain is connected to the N-terminus of the first light chain. This connection can be either directly via a bond or indirectly via a linker. In general the bonding between the domains can be achieved via any entity suitable to hold the different subunits together, comprising, besides others, direct linkage or linkage via a peptide-linker, via a chemical linker or via a disulfide bond. Said bond may be a cleavable or a non-cleavable bond. A cleavable bond is a bond which is cleavable by e.g. a sequence specific protease. A non-cleavable bond is a bond which is stable after cellular uptake, in other words, several LC domains connected by a non-cleavable bond remain bound to each other, even after translocation into the cytoplasm.

The terms "bond", "bonds" or "bonding" describe any possibility to connect the different polypeptide chains with each other. In one embodiment said bond is a chemical bond, e.g. covalent bond (e.g. disulfid-bond), polar covalent bond, ionic bond, coordinate covalent bond, bent bonds, 3c-2e and 3c-4-e bonds, one- and three-electron bonds, aromatic bond, metallic bond, intermolecular bonding, permanent dipole to permanent dipole bonding, hydrogen bond, instantaneous dipole to induced dipole (van der Waals) bonding and/or cation-pi interaction. As mentioned above, this definition encompasses direct bonds as well as indirect bonds via chemical linkers.

A "chemical linker" is defined herein as an molecule entity produced by chemical means, which is suitable to connect the different subunits of the polypeptide of the present invention. These chemical linkage can be achieved for example by bifunctional agents known in the art. In another embodiment the chemical linkage is achieved by di-sulfid bonds, similar to the connection between heavy and light chain in the wildtype. In yet another embodiment the introduction of a disulfide bond is achieved by introducing a cysteine containing sequence of the heavy chain (e.g. aa 449-459 of BoNT/A) into the light chain. Further non-limiting examples for such chemical linkers are carboxylic acids, ethoxylated polyhydric alcohol, polyvinyl pyrrolidone, polyethylene glycol etc.

A "peptide linker" is defined herein as a peptide of 1, 2, 3, 4, 5, 10, 20, 30, 40, 50, or up to 100 amino acids length, which connects the different subunits of the polypeptide of the present invention with each other. In one embodiment said peptide-linker comprises at least two cysteines. In another embodiment the linker comprises one, two, three, four, five, six, seven, eight, nine, ten or up to 20 histidines, in another embodiment the linker is a protease cleavage site. In a further embodiment the linker enables the production of the full fusion protein by recombinant methods.

In another embodiment a protease cleavage site can be introduced between the first and the second light chain, e.g. a site which can be cut by $E.\ coli$ proteases as they are listed for example in DE102005002978 but without the restriction to these proteases. In another embodiment the protease cleavage site is any of the recognition sites for either serine proteases (e.g. chymotrypsin, trypsin, elastase, subtilisin), threonine proteases, cysteine proteases (e.g. papain, cathepsin, caspase, calpain), aspartic acid proteases (e.g. HIV-protease, chymosin, renin, cathepsin, pepsin, plasmepsin), metalloproteases or glutamic acid proteases or any combination thereof.

The person skilled in the art will understand that this invention is not only suitable for the usage of wild-type heavy and light chain(s), but that also recombinant peptides and/or hybrid neurotoxic components are encompassed by this invention. Therefore, in one embodiment a fusion protein of at least one heavy chain, at least a first light chain and at least a second light chain is envisaged, wherein at least one, some or all of the used domains are produced recombinantly, in another embodiment hybrid peptides are used, i.e. peptides composed of sub-domains from different serotypes (e.g. a heavy, chain comprising a binding and a translocation domain of a different serotypes or even a different toxin, e.g. tetanus toxin, cholera toxin or pertussis toxin).

In another embodiment the light chain(s) of other clostridial toxins, e.g. *Clostridium bifermentans, Clostridium botulinum* of a different serotype, *Clostridium difficile, Clostridium histolyticum, Clostridium kluyveri, Clostridium novyi, Clostridium oedematiens, Clostridium perfringens, Clostridium ramosum, Clostridium sporogenes, Clostridium tetani, Clostridium tertium* or *Clostridium welchii* can be used, e.g. in one embodiment tetanus toxin (also called tetanospasmin or spasmogenic toxin) is used as well as any variations and serotype of the different toxins. In addition the cell binding part of the heavy chain can be exchanged with a polypeptide sequence which endows the fusion protein with another targeting domain i.e. another cell specificity (e.g. WO 2007/13839). Furthermore yet another embodiment of the invention makes use of heavy and light chains, which have been altered by molecular or biochemical methods, more preferably deletions, insertions, amino acid exchange or elongation.

In one embodiment the serotype of the translocation sub-domain of HC (i.e. the N-terminal part of the heavy chain) is the same sero-type like the one of the first LC.

In one embodiment the SNARE-complex cleaving ability of the LC-domain is of major interest. Therefore, in one embodiment one of the LC-domains of the fusion protein is exchanged by the IGA protease from *Neisseria gonorrhoeae*, which possesses SNARE-complex cleaving ability as well.

In further embodiments the present invention also refers to neurotoxins which are chemically modified, e.g. by pegylation, glycosylation, sulfatation, phosphorylation or any other modification, in particular of one or more surface or solvent exposed amino acid(s).

Furthermore, in another embodiment, the neurotoxin possesses a tag-sequence to allow for simplified purification methods. Such known labelling methods make use of small molecules or peptides, e.g. biotin, streptavidin, strep-tag, His-tag, antigens, antibody-fragments etc. which are covalently or non covalently bound to the polypeptide of the present invention and enable the purification via affinity-chromatgraphy, beads or other separation methods.

As stated above in some embodiments the fusion protein contains recombinant domains or is produced recombinantly in full. DNA-sequences of all heavy and light chains of all serotypes of botulinum toxin are available from public databases. Therefore, it is envisaged to construct vectors carrying the desired genes for the heavy and light chains by relying on these database information. The vector then is expressed in e.g. *E. coli* to produce a fusion protein. In another embodiment the vector can be expressed in other expression systems, like for example yeast, insect cells or CHO-cells. In another embodiment the protein domains are produced separately and then connected later by chemical methods. The resulting protein is then isolated by known methods of protein purification, then, if necessary, further processed (e.g. cleavage, chemical linkage or treatment) and used as an active agent in a pharmaceutical formulation.

In one embodiment the modified neurotoxin is additionally modified to alter (i.e. increase and decrease) its binding affinity to its receptor. Binding affinity may be determined in comparison to a native neurotoxin, i.e. a neurotoxin derived from *C. botulinum* and having a wild-type amino acid sequence. Alternatively, binding assays may be performed with a fragment of said neurotoxin. Preferably said neurotoxin is obtainable from *C. botulinum*. An increased affinity means that the neurotoxin according to the invention has a lower dissociation constant in comparison to the non-modified neuro-toxin. Preferably, the native neurotoxin is botulinum neurotoxin of serotype A including any subtype A, which is defined in detail below. A recombinantly produced botulinum neurotoxin of serotype A, whose amino acid sequence is identical to a botulinum neurotoxin obtained from *C. botulinum*, behaves pharmacologically identical or similar to the native botulinum neurotoxin obtained from *C. botulinum*. Such a recombinant neurotoxin may be produced in e.g. *E. coli* and is commonly referred to as "recombinant botulinum neuro-toxin". Binding assays may be performed with a neurotoxin isolated from *C. botulinum* or a neurotoxin obtained by recombinant protein expression. Preferably, the polypeptide, the active fragment or derivative according to the present invention binds specifically to plasma membrane associated molecules, transmembrane proteins, synaptic vesicle proteins, a protein of the synaptotagmin family or the synaptic vesicle glycoproteins 2 (SV2), preferably synaptotagmin I and/or synaptotagmin II and/or SV2A, SV2B or SV2C, particularly preferred human synaptotagmin I and/or human synaptotagmin II and/or human SV2A, SV2B or SV2C. The binding is preferably determined in vitro. The skilled person knows various assays for determining binding affinities between a first protein (the neurotoxin) and a second protein (the receptor). Any such assay may be useful for determining the effect of a mutation on receptor binding. One such assay is a GST-pull-down-assay, which is preferred in accordance with the teaching of the present invention. This assay is described in the examples of the present invention. Surface plasmon resonance may also be used to study the binding affinity. Experimental conditions therefore, are e.g. described in Yowler et al., Biochemistry 43 (2004), 9725-9731. In addition, the binding affinity may be assessed using isothermal microcalorimetry. In one embodiment the ganglioside-binding domain and/or the protein receptor binding-domain of the neurotoxin is modified such as to enhance the binding capacity compared to the wild-type neurotoxin from which the HC domain is derived. As reference it is referred to WO2006/027207 A1, WO 2006/114308 A1 and PCT/EP2008/006151 (EP 07 014 785.5) which are fully incorporated in this document.

In another embodiment, also isoforms, homologs, orthologs and paralogs of botulinum toxin are encompassed, which show at least 50%, at least 60%, at least 70%, at least 80%, at least 90% and up to 60%, up to 70%, up to 80%, up to 90%, up to 100% sequence identity. The sequence identity can be calculated by any algorithm suitable to yield reliable results, for example by using the FASTA algorithm (W. R. Pearson & D. J. Lipman PNAS (1988) 85:2444-2448). Sequence identity may be calculated by comparing two polypeptides or two domains such as two LC domains or fragments thereof.

In one embodiment the polypeptide of the invention is one of the following: LCBoNT/A-LCBoNT/A-HCBoNT/A, LCBoNT/C-LCBoNT/A-HCBoNT/A, LCBoNT/B-LCBoNT/A-HCBoNT/A, LCBoNT/A-LCBoNT/C—HCBoNT/C, LCBoNT/C-LCBoNT/C—HCBoNT/C, LCBoNT/B-LCBoNT/C—HCBoNT/C and LCTeNT-LCBoNT/A-HCBoNT/A.

Of these before mentioned modified neurotoxins especially the constructs with an additional light chain type A are to be mentioned, due to its excellent proteolytic activity and stability.

The invention also relates to an antibody able to specifically bind to the polypeptide of the present invention.

The term "antibody" is used herein for any protein or polypeptide, which is able to bind specific to the polypeptide of the invention (e.g. amino acids, primary, secondary or tertiary structure elements, epitopes, fragments, etc.). Examples for antibodies are the gamma-globulins IgA, IgD, IgE, IgG and IgM, fragments thereof, modified versions thereof, etc.; also any gene-product of the V, D, J genes, T-cell-receptors, B-cell-receptors, etc. Also included are single chain antibodies or modified antibodies such as humanized antibodies. Since antigens are just defined by its ability to be bound by an antibody, they represent a very heterogeneous group. Examples for "antigens" are proteins; oligopepeptides; sugars, lipids, lipopolysaccharides, cellular, viral or bacterial surface molecules; macromolecules, etc. The term "specific" describes a binding affinity high enough to differentiate between different structural patterns, i.e. the difference between the affinity for the antigen should be at least 10 times, 20 times, $10^2$ times, $10^3$ times, $10^4$ times, $10^5$ times, $10^6$ times, $10^7$ times, $10^8$ times, up to $10^9$ times higher then the affinity to a reference structure, which is not the antigen or epitope. In one embodiment, said reference structure is not the neurotoxin of serotype A to G. The antibody of the present invention is specific for the polypeptide of the present invention. In one embodiment it does not bind to the wild-type neuro-toxins (i.e. serotypes A to G) and/or other neurotoxins and/or neurotoxin fragments known in the art, in another embodiment said antibody binds with much reduced affinity to the wild-type neurotoxins and/or other neurotoxins known in the art, whereas the difference in affinity high enough, that the anti-body is still suitable for purification, toxin inactivation and/or detection methods. Examples for antibodies of this invention are such antibodies, which recognize the additional LC-domain(s) and/or modifications of the additional LC-domain(s).

Such antibodies may be produced by the known method in the art. Furthermore several methods are known how to positively and negatively select for antibodies, which recognize the polypeptide of the invention but not (or to a much lesser degree) known neurotoxins and/or fragments. As example reference is made to the documents WO2005/063817, WO2003/029458 and WO2002/086096 which are fully incorporated hereinunder.

Said antibody is in one embodiment suitable for purification, toxin inactivation and/or detection methods. Examples for the application of such antibodies are for example HDA (hemidiaphragma assay), immunoprecipitation, affinity-chromatography, western-blots, etc.

The invention also encompasses nucleic acids encoding the polypeptide of the invention. In one embodiment said nucleic acid contains additional sequences known in the art like e.g. promotors, enhancers, bacterial elements, IRES-regions, terminal capping structures etc. This nucleic acid molecule can be hnRNA, mRNA, RNA, DNA, PNA, LNA, and/or modified nucleic acid molecules etc. The nucleic acid can be circular, linear or integrated into a genome. Also DNA-concatemers coding for fusion proteins comprising three, four, five, six, seven, eight, nine or ten LC domains are encompassed.

The invention also encompasses a vector suitable for in vitro and/or in vivo expression of the polypeptide of the present invention. Whereas in vivo the vector can be transient and/or stable expressed. In one embodiment the vector furthermore comprises regulatory elements and/or selection markers. Said vector in one embodiment is based on virus origin, in another embodiment of phage origin, in yet another embodiment of bacterial origin.

The invention also encompasses prokaryotic and/or eukaryotic host cells suitable to express said vector and in particular the polypeptide of the invention. In one embodiment said host cell is of clostridial origin, in another embodiment said host cell is derived from standard cells for recombinant expression, e.g. E. coli, etc. In one embodiment, the polypeptide is modified inside the host cell (i.e. glycosylated, phosphorylated, processed by proteases, etc.). Therefore, both the pre-polypeptide, any intermediate protein product as well as the final polypeptide are encompassed by this invention.

The polypeptide of the invention may be part of a composition or a pharmaceutical composition. A "pharmaceutical composition" is a formulation in which an active ingredient for use as a medicament or a diagnostic is contained or comprised. Such pharmaceutical composition may be suitable for diagnostic or therapeutic administration (i.e. by intramuscular or subcutaneous injection) to a human patient.

This pharmaceutical composition to be used herein may comprise the polypeptide of the invention (i.e. the modified neurotoxic component) as the sole active component or may contain additional pharmaceutically active components e.g. a hyaluronic acid or a polyvinylpyrrolidone or a polyethlenegycol, such composition being optionally pH stabilized by a suitable pH buffer, in particular by a sodium acetate buffer, and/or a cryoprotectant polyalcohol.

Within one embodiment of the present invention it is envisaged that the pharmaceutical formulation contains no proteins found in the botulinum toxin complex other than the neurotoxic component which is part of the polypeptide of the present invention. The precursor of the polypeptide of the present invention may be cleaved or uncleaved, however, within an embodiment of particular interest the precursor has been cleaved into the heavy and the light chains. As pointed out above, the polypeptides may be of wild-type sequence or may be modified at one or more residues. Modification comprises chemical modification e.g. by glycosylation, acetylation, acylation or the like, which may be beneficial e.g. to the uptake or stability of the polypeptide. The polypeptide chain of the polypeptide of the invention may, however, alternatively or additionally be modified by addition, substitution or deletion of one or more amino acid residues.

In one embodiment, the polypeptide of the invention has a biological activity of 10 to 500 $LD_{50}$ units per ng polypeptide of the invention, as determined in a mouse $LD_{50}$ assay. In another embodiment, the polypeptide of the invention has a biological activity of about 150 $LD_{50}$ units per nanogram. Generally, the pharmaceutical composition of the present invention comprises the polypeptide of the invention in a quantity of about 6 pg to about 30 ng.

A pharmaceutical composition comprising the neurotoxic component of botulinum toxin type A in isolated form is commercially available in Germany from Merz Pharmaceuticals GmbH under the trademark XEOMIN®. The production of the neurotoxic component of botulinum toxin type A and B are described, for example, in the international patent applications WO 00174703 and WO 2006/133818. The skilled person can adapt said compositions to the polypeptide of the invention referred herein.

In one embodiment, said composition is a reconstituted solution of the polypeptide of the invention. In another embodiment the composition further comprises sucrose or human serum albumin or both, still another embodiment the ratio of human serum albumin to sucrose is about 1:5. In another embodiment, said human serum albumin is recombinant human serum albumin. Alternatively, said composition is free of mammalian derived proteins such as human serum albumin. Any such solution may provide sufficient neurotoxin stability by replacing serum albumin with other non-proteinaceous stabilizers (infra).

Within the present patent application, the use of a medicament based on the modified neurotoxic component mentioned above can be used.

With regard to the composition and dosing of the medicament on the basis of botulinum toxin, and in regard to the composition, dosing and frequency of administration of the medicament on the basis of the neurotoxic component of botulinum toxin, reference is made to PCT/EP2007/005754.

The pharmaceutical composition may be lyophilized or vacuum dried, reconstituted, or may prevail in solution. When reconstituted, in one embodiment the reconstituted solution is prepared adding sterile physiological saline (0.9% NaCl).

Such composition may comprise additional excipients. The term "excipient" refers to a substance present in a pharmaceutical composition other than the active pharmaceutical ingredient present in the pharmaceutical composition. An excipient can be a buffer, carrier, antiadherent, analgesic, binder, disintegrant, filler, diluent, preservative, vehicle, cyclodextrin and/or bulking agent such as albumin, gelatin, collagen, sodium chloride, preservative, cryoprotectant and/or stabilizer.

A "pH buffer" refers to a chemical substance being capable to adjust the pH value of a composition, solution and the like to a certain value or to a certain pH range. In one embodiment this pH range can be between pH 5 to pH 8, in another embodiment pH 7 to pH 8, in yet another embodiment 7,2 to 7,6, and in yet a further embodiment a pH of 7,4. In another embodiment the pharmaceutical composition has a pH of between about 4 and 7.5 when reconstituted or upon injection, in yet another embodiment about pH 6.8 and pH 7.6 and in a further embodiment between pH 7.4 and pH 7.6.

In one embodiment the composition also contains a 1-100 mM, in another embodiment 10 mM sodium acetate buffer.

The pH ranges given mentioned above are only typical examples and the actual pH may include any interval between the numerical values given above. Suitable buffers which are in accordance with the teaching of the present invention are e.g. sodium-phosphate buffer, sodium-acetate buffer, TRIS buffer or any buffer, which is suitable to buffer within the above pH-ranges.

"Stabilizing", "stabilizes" or "stabilization" means that the active ingredient, i.e., the polypeptide of the invention in a reconstituted or aqueous solution pharmaceutical composition has greater than about 20%, 30%, 40%, 50%, 60%, 70%, 80%, 90%, and up to about 100% of the toxicity that the biologically active polypeptide of the invention had prior to being incorporated into the pharmaceutical composition.

Examples of such stabilizers are gelatin or albumin, in one embodiment of human origin or obtained from a recombinant source. Proteins from non-human or non-animal sources are also included. The stabilizers may be modified by chemical means or by recombinant genetics. In one embodiment of the present invention, it is envisaged to use alcohols, e.g., inositol, mannitol, as cryoprotectant excipients to stabilize proteins during lyophilization.

In another embodiment of the present invention, the stabilizer ray be a non proteinaceous stabilizing agent comprising a hyaluronic acid or a polyvinylpyrrolidone (KOLLIDON®, polvinyipyrrolidone), hydroxyethyl starch, alginate or a polyethylene glycol or any combination thereof, such composition being optionally pH stabilized by a suitable pH buffer, in particular by a sodium acetate buffer, or a cryoprotectant or both. Said composition may comprise in addition to the mentioned stabilizers water and at least one polyalcohol, such as mannitol or sorbitol or mixtures thereof. It may also comprise mono-, di- or higher polysaccharides, such as glucose, sucrose or fructose. Such composition is considered to be a safer composition possessing remarkable stability.

The hyaluronic acid in the instant pharmaceutical composition is in one embodiment combined with the polypeptide of the invention in a quantity of 0.1 to 10 mg, especially 1 mg hyaluronic acid per ml in a 200 U/ml botulinum toxin solution.

The polyvinylpyrrolidone (KOLLIDON®) when present in the instant composition, is combined with the polypeptide of the invention in such a quantity to provide a reconstituted solution comprising 10 to 500 mg, especially 100 mg polyvinylpyrrolidone per ml in a 200 U/ml polypeptide of the invention solution. In another embodiment reconstitution is carried out in up to8 ml solution. This results in concentrations of down to 12.5 mg polyvinylpyrrolidone per ml in a 25 U/ml polypeptide of the invention solution.

The polyethyleneglycol in the instant pharmaceutical composition is in one embodiment combined with the polypeptide of the invention in a quantity of 10 to 500 mg, especially 100 mg polyethyleneglycol per ml in a 200 U/ml botulinum toxin solution. In another embodiment, the subject solution also contains a 1-100 mM, in yet another embodiment 10 mM sodium acetate buffer.

The pharmaceutical composition in accordance with the present invention in one embodiment retains its potency substantially unchanged for six month, one year, two year, three year and/or four year periods when stored at a temperature between about +8° C. and about −20° C. Additionally, the indicated pharmaceutical compositions may have a potency or percent recovery of between about 20% and about 100% upon reconstitution.

"Cryoprotectant" refers to excipients which result in an active ingredient, i.e. the polypeptide of the invention in a reconstituted or aqueous solution pharmaceutical composition that has greater than about 20%, 30%, 40%, 50%, 60%, 70%, 80%, 90%, and up to about 100% of the toxicity that the biologically active polypeptide of the invention had prior to being freeze-dried in the pharmaceutical composition.

In another embodiment, the composition may contain a polyhydroxy compound, e.g. a polyalcohol as cryoprotectant. Examples of polyalcohols that might be used include, e.g., inositol, mannitol and other non-reducing alcohols. Some embodiments of the composition do not comprise a proteinaceous stabilizer, or do not contain trehalose or maltotriose or lactose or sucrose or related sugar or carbohydrate compounds which are sometimes used as cryoprotectants.

The terms "preservative" and "preservatives" refer to a substance or a group of substances, respectively, which prevent the growth or survival of microorganisms, insects, bacteria or other contaminating organisms within said composition. Preservatives also prevent said composition from undesired chemical changes. Preservatives which can be used in the scope of this patent are all preservatives of the state of the art known to the skilled person. Examples of preservatives that might be used include, inter alia, e.g. benzylic alcohol, benzoic: acid, benzalkonium chloride, calcium propionate, sodium nitrate, sodium nitrite, sulphites (sulfur dioxide, sodium bisulfite, potassium hydrogen sulfite, etc.), disodium EDTA, formaldehyde, glutaraldehyde, diatomaceous earth, ethanol, methyl chloroisothiazolinone, butylated hydroxyanisole and/or butylated hydroxytoluene.

The term "analgesic" relates to analgesic drugs that act in various ways on the peripheral and central nervous systems and includes inter alia PARACETAMOL® (PARACETAMOL®, acetaminophen), the nonsteroidal anti-inflammatory drugs (NSAIDs) such as the salicylates, narcotic drugs such as morphine, synthetic drugs with narcotic properties such as TRAMADOL® (TRAMADOL®, an opioid analgesic), and various others. Also included is any compound with a local analgesic effect such as e.g. lidocaine, benzylic alcohol, benzoic acid and others.

In one embodiment the analgesic is part of the composition, in another embodiment, the analgesic is administered before, during or after the treatment with the chemodenervating agent.

The term "lyophilization" is used in this document for a treatment of a solution containing the polypeptide of the invention, whereas this solution is frozen and dried until only the solid components of the composition are left over. The freeze-dried product of this treatment is therefore defined in this document as "lyophilisate".

In this document the term "reconstitution" is defined as the process of solubilization of said freeze-dried composition of the polypeptide of the invention. This can be done by adding the appropriate amount of sterile water, e.g. if all necessary components are already contained in the lyophilisate. Or, if this is not the case, it can be done e.g. by adding a sterile saline-solution alone or if applicable with the addition of components comprising e.g. a pH buffer, excipient, cryoprotectant, preservative, analgesic stabilizer or any combination thereof. The saline of before mentioned "saline-solution" is a salt-solution, e.g. a sodium-chloride (NaCl) solution, or an isotonic sodium-chloride solution (i.e. a sodium-chloride concentration of 0,9%). The solubilization is carried out in such a manner that the final "reconstitution" is directly or indirectly, i.e. for example after dilution, administrable to the patient. The neurotoxin may be reconstituted in isotonic media, e.g. in isotonic saline or sterile saline.

It is noteworthy that the concept of the present invention, which involves the administration of the polypeptide of the invention, for the treatment of any condition which is associated with hyperactive cholinergic innervation of a muscle or an exocrine gland, where the polypeptide of the invention blocks acetylcholine secretion into the synaptic cleft. Therefore, treatment offered by the present invention may be directed at any of the following indications, most of which are described in detail in Dressler D (2000) (Botulinum Toxin Therapy. Thieme Verlag, Stuttgart, New York):

dystonia
    cranial dystonia
        blepharospasm
        oromandibular dystonia
            jaw opening type
            jaw closing type
        bruxism
        Meige syndrome
        lingual dystonia
        apraxia of eyelid opening
    cervical dystonia
        antecollis
        retrocollis
        laterocollis
        torticollis
    pharyngeal dystonia
    laryngeal dystonia
        spasmodic dysphonia/adductor type
        spasmodic dysphonia/abductor type
        spasmodic dyspnea
    limb dystonia
        arm dystonia
            task specific dystonia
                writer's cramp
                musician's cramps
                golfer's cramp
        leg dystonia
            thigh adduction, thigh abduction
            knee flexion, knee extension
            ankle flexion, ankle extension
            equinovarus deformity
        foot dystonia
            striatal toe
            toe flexion
            toe extension
    axial dystonia
        pisa syndrome
        belly dancer dystonia
    segmental dystonia
    hemidystonia
    generalised dystonia
dystonia in lubag
dystonia in corticobasal degeneration
dystonia in lubag
tardive dystonia
dystonia in spinocerebellar ataxia
dystonia in Parkinson's disease
dystonia in Huntington's disease
dystonia in Hallervorden Spatz disease
dopa-induced dyskinesias/dopa-induced dystonia
tardive dyskinesias/tardive dystonia
paroxysmal dyskinesias/dystonias
    kinesiogenic
    non-kinesiogenic
    action-induced
palatal myoclonus
myoclonus
myokymia
rigidity
benign muscle cramps
hereditary chin trembling
paradoxic jaw muscle activity
hemimasticatory spasms
hypertrophic branchial myopathy
maseteric hypertrophy
tibialis anterior hypertrophy
nystagmus
oscillopsia
hyperhydrosis
supranuclear gaze palsy
epilepsia partialis continua
planning of spasmodic torticollis operation
abductor vocal cord paralysis
recalcitrant mutational dysphonia
upper oesophageal sphincter dysfunction
vocal fold granuloma
stuttering
Gilles de la Tourette syndrom
middle ear myoclonus
protective larynx closure
postlaryngectomy speech failure
protective ptosis
entropion
sphincter Odii dysfunction
pseudoachalasia
nonachalsia oesophageal motor disorders
vaginismus
postoperative immobilisation
tremor
genito-urinary diseases
    bladder dysfunction
        overactive bladder
            urinary incontinence
            urinary retention
            spastic bladder
gastro-intestinal diseases
detrusor sphincter dyssynergia
bladder sphincter spasm
hemifacial spasm
reinnervation dyskinesias
cosmetic use
crow's feet
    frowning
    facial asymmetries
    mentalis dimples -continued glabella frown line
  frontal lines
  platysma
  smoker's lines
  marionette lines
  masseter lift
 stiff person syndrome
 tetanus
 prostate diseases
  prostate hyperplasia
  prostate cancer
 adipositas treatment
 infantile cerebral palsy
 strabismus
  mixed
  paralytic
  concomitant
  after retinal detachment surgery
  after cataract surgery
  in aphakia
  myositic strabismus
  myopathic strabismus
  dissociated vertical deviation
  as an adjunct to strabismus surgery
  esotropia
  exotropia
 achalasia
 anal fissures
 exocrine gland hyperactivity
 Frey syndrome
 Crocodile Tears syndrome
 hyperhidrosis
  axillar
  palmar
  plantar
 rhinorrhea
 relative hypersalivation
  in stroke
  in parkinsosn's
  in amyotrophic lateral sclerosis
 spastic conditions
  in encephalitis and myelitis
   autoimmune processes
    multiple sclerosis
    transverse myelitis
    Devic syndrome
   viral infections
   bacterial infections
   parasitic infections
   fungal infections
  in hereditary spastic paraparesis
  postapoplectic syndrome
   hemispheric infarction
   brainstem infarction
   myelon infarction
  in central nervous system trauma
   hemispheric lesions
   brainstem lesions
   myelon lesion
  in central nervous system hemorrhage
   intracerebral hemorrhage
   subarachnoidal hemorrhage
   subdural hemorrhage
   intraspinal hemorrhage
  in neoplasias
   hemispheric tumors
   brainstem tumors
   myelon tumors
 headache
  migraine
  tension headache
  sinus headache
  chronic headache
 and/or hair loss.

The pharmaceutical composition comprising the botulinum toxin is administered, in one embodiment several times, in an effective amount for improving the patient's condition. It also has to be noted that depending on the persistency of the polypeptide of the invention lower or higher dosages are needed, therefore, the following dosing references are just for orientation purpose.

Typically, the dose administered to the patient will be up to about 1000 units, but in general should not exceed 400 units per patient. In one embodiment the range lies between about 80 to about 400 units. These values are in one embodiment valid for adult patients. For children, the respective doses range from 25 to 800 and in another embodiment from 50 to 400 units.

While the above ranges relate to the maximum total doses, the dose range per muscle is in one embodiment within 3 to 6 units/kg body weight (b.w.), for small muscles 0, 5-2 U/kg b.w., in another embodiment 0,1-1 U/kg b.w. Generally doses should not exceed 50 Upper injection site and 100 Upper muscle.

In one embodiment of the present invention the effective amount of botulinum toxin administered exceeds 500 U of polypeptide of the invention in adults or exceeds 15 U/kg body weight in children.

As to the frequency of dosing, the re-injection interval depend greatly on the persistency of the modified neurotoxin. Thus, according to the present invention the medicament to be administered is re-administered in intervals of between 3 and 6 months, in another embodiment the medicament is re-administered in intervals of between 2 weeks and less than 3 months. However, depending on the modifications of the neurotoxin, in other embodiments treatments of more than 6 months up to 12 months or treatments in time periods shorter than 2 weeks are envisaged.

With regard to the composition and dosing of the medicament on the basis of botulinum toxin, and in regard to the composition, dosing and frequency of administration of the medicament on the basis of the neurotoxic component of botulinum toxin, U.S. 60/817,756 is incorporated herein by reference.

While the above stated values are to be understood as a general guideline for administering the medicament as used within the present invention, it is, however, ultimately the physician who is responsible for the treatment who decides on both the quantity of toxin administered and the frequency of its administration.

The medicament on the basis of botulinum toxin can be injected directly into the affected muscle. In order to find the appropriate injection site, several means exist which help the physician in order to find the same. Within the present invention, all methods for finding the best injection site are applicable, such as injection guided by electromyography (EMG), injection guided by palpation, injection guided by CT/MRI, as well as injection guided by sonography (ultra-sound). Among those methods, the latter is in one embodiment the method of choice when treating children. With respect to further details regarding the injection guided by sonography, we refer to Berweck "Sonography-guided injection of botulinum toxin A in children with cerebral palsy", *Neuropediatric* 2002 (33), 221-223.

The term "injection" is defined as any process, which allows the person skilled in the art to administer the active agent to the target site by penetrating the skin. An incomplete number of examples for "injections" are subcutaneous, intramuscular, intra-venous, intra-thecal, intra-arterial, etc.

It is to be understood that the terminology used herein is for the purpose of describing particular embodiments only and is not intended to be limiting. It must be noted that, as used in the specification and the appended claims, the singular forms "a", "an" and "the" include plural referents unless the context clearly dictates otherwise.

Literature:

de Paiva A, Meunier F A, Molgo J, Aoki K R, Dolly J O. Related Articles, Functional repair of motor endplates after botulinum neurotoxin type A poisoning: biphasic switch of synaptic activity between nerve sprouts and their parent terminals. Proc Natl Acad Sci USA. 1999; 96(6):3200-5.

E. L. V. Harris (Ed.), S. Angal (Ed.), "Protein Purification Methods: A Practical Approach", Oxford University Press (December 1989), ISBN-10: 019963002X, ISBN-13: 978-0199630028

Eleopra R, Tugnoli V, Quatrale R, Gastaldo E, Rossetto O, De Grandis D, Montecucco C. Botulinum neurotoxin serotypes A and C do not affect motor units survival in humans: an electrophysiological study by motor units counting. Clin Neurophysiol. 2002; 113(8):1258-64.

Eleopra R, Tugnoli V, Rossetto O, Montecucco C, De Grandis D. Botulinum neurotoxin serotype C: a novel effective botulinum toxin therapy in human. Neurosci Lett. 1997; 224(2):91-4.

Foran P G, Mohammed N, Lisk G O, Nagwaney S, Lawrence G W, Johnson E, Smith L, Aoki K R, Dolly J O. Evaluation of the therapeutic usefulness of botulinum neurotoxin B, C1, E, and F compared with the long lasting type A. Basis for distinct durations of inhibition of exocytosis in central neurons. J Biol. Chem. 2003 Jan. 10; 278(2):1363-71. [Epub 2002 Oct. 14]

John M. Walker, Humana Press; "The Protein Protocols Handbook (Methods in Molecular Biology)", Volume: 2 (February 2002), ISBN-10: 0896039404, ISBN-13: 978-0896039407

Jurasinski C V, Lieth E, Dang Do A N, Schengrund CL Correlation of cleavage of SNAP-25 with muscle function in a rat model of Botulinum neurotoxin type A induced paralysis Toxicon. 2001; 39(9):1309-15

Robert K. Scopes, "Protein Purification: Principles and Practice", Verlag: Springer, Berlin; Auflage: 3 Sub (January 1994), ISBN-10: 0387940723, ISBN-13: 978-0387940724

The present invention is now further exemplified by way of the non-limited examples recited herein under.

EXAMPLES

Example 1

Construction of an Expression plasmid

The DNA-sequence of the heavy chain of botulinum toxin A is amplified from chomosomal DNA of C. botulinum Type A (database No. AAA23262) by PCR. At the 5' end a sequence is added coding for the recognition sequence of thrombin. At the 3' end a DNA sequence is added, coding for an affinity tag peptide, suitable for later purification (e.g. His-tag or Strep-tag). The DNA is inserted into an expression plasmid. The DNA sequences for the first and second light chain are also of serotype A and are amplified in a similar fashion from chromosomal DNA of C. botulinum type A (database No. AAA23262) via PCR. The sequence of the light chain is then introduced twice consecutively in the expression plasmid upstream of the thrombin recognition sequence (TE). In total therefore the sequences shows the following coding structure: LC-LC-TE-HC-Tag.

Example 2

Production of the fusion protein in E.Coli

The fusion protein is transfected into E.coli TG1. The induction is performed at 21° C. for 4 hours. The fusion protein is then purified via STREP-TACTIN® SEPHAROSE® (STREP-TACTIN® SEPHAROSE®, agarose-based matrix for purification of recombinant Strep-tagged proteins; IBA GmbH, Göttingen) column chromatography according to manufacturers protocol. The fusion protein then is activated by immobilized thrombin (Thrombin SEPHAROSE® agarose-based matrix) which cleaves the peptide linkage between the heavy chain and the two light chains. The subunits of the protein remain only connected via disulfide bonds.

Example 3

Test of Persistency (Extensor Digitorum Brevis, EDB)

A test person is applied with 4 units Xeomin® (Merz Pharmaceuticals GmbH) into the right EDB solubilized in 0,1 ml physiological saline and into the left EDB 4 units of a modified botulinum toxin (fusion protein of botulinum toxin type A conjugated with an additional light chain of botulinum toxin type A). Each 30 days the "compound muscle action potential" (CMAP) is electrophysiological measured. After 90 days the amplitude of the CMAP of the right EDB is reduced about 40% (in comparison to the starting activity) whereas in the EDB on the left side the amplitude is reduced at about 70%. On the left side the CMAP reaches 40% after 150 days.

Example 4

Prolongation of persistency

A patient suffering from torticoilis spasmodicus is treated with BOTOX® (Allergan, Inc.) (240 units). He has to be treated every 10 to 12 weeks in a neurological office due to a decreased activity of the botulinum toxin. The patient then receives an injection of 240 units of a modified neurotoxin (botulinum toxin type A with an additional fused light chain of botulinum toxin type A). The patient needs no further injection till 18 weeks after the first treatment.

The invention claimed is

1. A polypeptide comprising:
   (a) a heavy chain (HC) domain of a neurotoxic component of a clostridial toxin;
   (b) a first light chain (LC) domain of a neurotoxic component of a clostridial toxin; and
   (c) at least one further LC domain of a neurotoxic component of a clostridial toxin;
   wherein the domains are connected by a direct linkage via a covalent bond, a peptide-linker, a chemical linker, or a combination of two or more thereof, and wherein the first and at least one further LC domains may be the same or different from each other, and wherein each of the first and at least one further LC domains exhibit proteolytic activity.

2. The polypeptide of claim 1, wherein the HC domain, the first LC domain, or the at least one further LC domain comprise at least one modification selected from the group consisting of a phosphorylation, a pegylation, a glycosylation, a sulfatation, a methylation, an acetylation, a lipidation, a myristoylation, a palmitoylation, an isoprenylation, a linkage of glucosyl-phophatidylinositol, a hydroxylation, an amidation, and a tag-sequence.

3. The polypeptide of claim 1, wherein both the HC domain and an LC domain comprise at least one modification selected from the group consisting of a phosphorylation, a pegylation, a glycosylation, a sulfatation, a methylation, an acetylation, a lipidation, a myristoylation, a palmitoylation, an isoprenylation, a linkage of glucosyl-phophatidylinositol, a hydroxylation, an amidation, and a tag-sequence.

4. The polypeptide of claim 1, wherein the polypeptide is selected from Light Chain Botulinum neurotoxin type A-Light Chain Botulinum neurotoxin type A-Heavy Chain Botulinum neurotoxin type A (LCBoNT/A-LCBoNT/A-HCBoNT/A); Light Chain Botulinum neurotoxin type C-Light Chain Botulinum neurotoxin type A-Heavy Chain Botulinum neurotoxin type A (LCBoNT/C-LCBoNT/A-HCBoNT/A); Light Chain Botulinum neurotoxin type B-Light Chain Botulinum neurotoxin type A-Heavy Chain Botulinum neurotoxin type A (LCBoNT/B-LCBoNT/A-HCBoNT/A); Light Chain Botulinum neurotoxin type A-Light Chain Botulinum neurotoxin type C-Heavy Chain Botulinum neurotoxin type C (LCBoNT/A-LCBoNT/C-HCBoNT/C); Light Chain Botulinum neurotoxin type C-Light Chain Botulinum neurotoxin type C-Heavy Chain Botulinum neurotoxin type C (LCBoNT/C-LCBoNT/C-HCBoNT/C); Light Chain Botulinum neurotoxin type B-Light Chain Botulinum neurotoxin type C-Heavy Chain Botulinum neurotoxin type C (LCBoNT/B-LCBoNT/C-HCBoNT/C); and Light Chain Tetanus neurotoxin-Light Chain Botulinum neurotoxin type A-Heavy Chain Botulinum neurotoxin type A (LCTeNT-LCBoNT/A-HCBoNT/A).

5. A composition comprising the polypeptide of claim 1.

6. The composition of claim 5 further comprising a pharmaceutically acceptable carrier.

7. The composition of claim 5 further comprising a pH buffer, an excipient, a cryoprotectant, a preservative, an analgesic, a stabilizer or any combination thereof.

8. A method of treating a human or animal afflicted with a condition treatable with a *Clostridium botulinum* toxin, comprising administering to the human or animal, a treatment effective amount of the polypeptide of claim 1.

9. The method of claim 8, wherein the condition treatable with a *Clostridium botulinum* toxin is a cosmetic condition.

10. The method of claim 8, wherein the condition treatable with a *Clostridium botulinum* toxin is associated with hyperactive cholinergic innervations of a muscle or an exocrine gland.

11. The method of claim 8, wherein the polypeptide blocks acetylcholine secretion into the synaptic cleft.

* * * * *

UNITED STATES PATENT AND TRADEMARK OFFICE
CERTIFICATE OF CORRECTION

PATENT NO. : 8,748,151 B2  Page 1 of 1
APPLICATION NO. : 12/737895
DATED : June 10, 2014
INVENTOR(S) : Frevert It is certified that error appears in the above-identified patent and that said Letters Patent is hereby corrected as shown below:

On the Title Page, Item [30] Foreign Patent Doc., column 2, Line 67: delete "WO 02008609" and insert --WO 020086096--.

On Title Page 2, Item [56] References Cited, column 1, Line 1: should read "Japanese Office Action and English translation from JP20110524268 mailed 03 September 2013".

Signed and Sealed this
Fourth Day of November, 2014

Michelle K. Lee
*Deputy Director of the United States Patent and Trademark Office*

SEQUENCE LISTING

<160> NUMBER OF SEQ ID NOS: 13

<210> SEQ ID NO 1
<211> LENGTH: 7
<212> TYPE: PRT
<213> ORGANISM: Artificial Sequence
<220> FEATURE:
<223> OTHER INFORMATION: Clostridial Neurotoxin Amino Acid Sequence

<400> SEQUENCE: 1

Phe Glu Phe Tyr Lys Leu Leu
1               5

<210> SEQ ID NO 2
<211> LENGTH: 7
<212> TYPE: PRT
<213> ORGANISM: Artificial Sequence
<220> FEATURE:
<223> OTHER INFORMATION: Clostridial Neurotoxin Amino Acid Sequence

<400> SEQUENCE: 2

Glu Glu Lys Arg Ala Ile Leu
1               5

<210> SEQ ID NO 3
<211> LENGTH: 7
<212> TYPE: PRT
<213> ORGANISM: Artificial Sequence
<220> FEATURE:
<223> OTHER INFORMATION: Clostridial Neurotoxin Amino Acid Sequence

<400> SEQUENCE: 3

Glu Glu Lys Met Ala Ile Leu
1               5

<210> SEQ ID NO 4
<211> LENGTH: 7
<212> TYPE: PRT
<213> ORGANISM: Artificial Sequence
<220> FEATURE:
<223> OTHER INFORMATION: Clostridial Neurotoxin Amino Acid Sequence

<400> SEQUENCE: 4

Ser Glu Arg Asp Val Leu Leu
1               5

<210> SEQ ID NO 5
<211> LENGTH: 7
<212> TYPE: PRT
<213> ORGANISM: Artificial Sequence
<220> FEATURE:
<223> OTHER INFORMATION: Clostridial Neurotoxin Amino Acid Sequence

<400> SEQUENCE: 5

Val Asp Thr Gln Val Leu Leu
1               5

<210> SEQ ID NO 6
<211> LENGTH: 7
<212> TYPE: PRT
<213> ORGANISM: Artificial Sequence
<220> FEATURE:
<223> OTHER INFORMATION: Clostridial Neurotoxin Amino Acid Sequence

<400> SEQUENCE: 6

Ala Glu Val Gln Ala Leu Leu
1               5

<210> SEQ ID NO 7
<211> LENGTH: 7
<212> TYPE: PRT

```
<213> ORGANISM: Artificial Sequence
<220> FEATURE:
<223> OTHER INFORMATION: Clostridial Neurotoxin Amino Acid Sequence

<400> SEQUENCE: 7

Ser Asp Lys Gln Asn Leu Leu
1               5

<210> SEQ ID NO 8
<211> LENGTH: 7
<212> TYPE: PRT
<213> ORGANISM: Artificial Sequence
<220> FEATURE:
<223> OTHER INFORMATION: Clostridial Neurotoxin Amino Acid Sequence

<400> SEQUENCE: 8

Ser Asp Arg Gln Asn Leu Ile
1               5

<210> SEQ ID NO 9
<211> LENGTH: 7
<212> TYPE: PRT
<213> ORGANISM: Artificial Sequence
<220> FEATURE:
<223> OTHER INFORMATION: Clostridial Neurotoxin Amino Acid Sequence

<400> SEQUENCE: 9

Ala Asp Thr Gln Val Leu Met
1               5

<210> SEQ ID NO 10
<211> LENGTH: 7
<212> TYPE: PRT
<213> ORGANISM: Artificial Sequence
<220> FEATURE:
<223> OTHER INFORMATION: Clostridial Neurotoxin Amino Acid Sequence

<400> SEQUENCE: 10

Ser Asp Lys Gln Thr Leu Leu
1               5

<210> SEQ ID NO 11
<211> LENGTH: 7
<212> TYPE: PRT
<213> ORGANISM: Artificial Sequence
<220> FEATURE:
<223> OTHER INFORMATION: Clostridial Neurotoxin Amino Acid Sequence

<400> SEQUENCE: 11

Ser Gln Ile Lys Arg Leu Leu
1               5

<210> SEQ ID NO 12
<211> LENGTH: 7
<212> TYPE: PRT
<213> ORGANISM: Artificial Sequence
<220> FEATURE:
<223> OTHER INFORMATION: Clostridial Neurotoxin Amino Acid Sequence

<400> SEQUENCE: 12

Ala Asp Thr Gln Ala Leu Leu
1               5

<210> SEQ ID NO 13
<211> LENGTH: 7
<212> TYPE: PRT
<213> ORGANISM: Artificial Sequence
<220> FEATURE:
```

```
<223> OTHER INFORMATION: Clostridial Neurotoxin Amino Acid Sequence

<400> SEQUENCE: 13

Asn Glu Gln Ser Pro Leu Leu
1               5
```